(12) United States Patent
Mårup Osmundsen et al.

(10) Patent No.: US 9,926,247 B2
(45) Date of Patent: Mar. 27, 2018

(54) PROCESS FOR THE PREPARATION OF ETHYLENE GLYCOL FROM SUGARS

(71) Applicant: Haldor Topsøe A/S, Kgs. Lyngby (DK)

(72) Inventors: Christian Mårup Osmundsen, Gentofte (DK); Esben Taarning, Frederiksberg (DK); Martin Spangsberg Holm, Oxford (GB)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 15/321,301

(22) PCT Filed: Jun. 29, 2015

(86) PCT No.: PCT/EP2015/064693
§ 371 (c)(1),
(2) Date: Dec. 22, 2016

(87) PCT Pub. No.: WO2016/001136
PCT Pub. Date: Jan. 7, 2016

(65) Prior Publication Data
US 2017/0197893 A1    Jul. 13, 2017

(30) Foreign Application Priority Data
Jun. 30, 2014  (EP) .................................. 14174977

(51) Int. Cl.
C07C 27/00 (2006.01)
C07C 29/145 (2006.01)
C07C 45/60 (2006.01)
C07C 31/20 (2006.01)
C07C 29/141 (2006.01)

(52) U.S. Cl.
CPC ............ C07C 29/141 (2013.01); C07C 27/00 (2013.01); C07C 29/145 (2013.01); C07C 45/60 (2013.01)

(58) Field of Classification Search
CPC ... C07C 45/673; C07C 29/141; C07C 29/145; C07C 31/202; C07C 31/205; C07C 47/127; B01J 23/8896; B01J 23/892
See application file for complete search history.

(56) References Cited

U.S. PATENT DOCUMENTS 4,321,414 A    3/1982  Costa
2015/0329449 A1* 11/2015 Schreck .................. B01J 21/02
                                                  568/863

FOREIGN PATENT DOCUMENTS

DE         373975 C       4/1923
WO    WO 2005/058788 A1   6/2005

OTHER PUBLICATIONS

R. Ooms et al., "Conversion of Sugars to Ethylene Glycol with Nickel Tungsten Carbide in a Fed-Batch Reactor: High Productivity and Reaction Network Elucidation", Green Chemistry, vol. 16, 2014, pp. 695-707.

* cited by examiner

*Primary Examiner* — Jafar Parsa
(74) *Attorney, Agent, or Firm* — Blank Rome LLP

(57) ABSTRACT

A process for the preparation of ethylene glycol comprising the steps of hydrogenating a composition comprising $C_2$-oxygenate compounds in the gas phase in the presence of a catalyst.

22 Claims, No Drawings

PROCESS FOR THE PREPARATION OF ETHYLENE GLYCOL FROM SUGARS

BACKGROUND

Ethylene glycol can be prepared by a variety of routes including from sugars, e.g. monosaccharides, via fermentation and hydrogenolysis processes, or by hydroformylation.

The fermentation route is a five-step process wherein glucose is fermented to ethanol and carbon dioxide, followed by conversion of ethanol to ethylene, ethylene to ethylene oxide and ethylene oxide to ethylene glycol. One disadvantage of this method is that per mole of glucose fermented, two moles of carbon dioxide are produced together with two moles of ethanol; this has the effect that a theoretical maximum 67% of the carbon present in the glucose can be transformed to ethanol.

The hydrogenolysis route is a two-step process wherein glucose is reduced to sorbitol followed by hydrogenolysis of sorbitol to ethylene glycol, as illustrated by U.S. Pat. No. 6,297,409 B1 and US 2008/0228014 A1. Significant quantities of propylene glycol, compared to ethylene glycol, are formed via the hydrogenolysis process. Additionally, the amount of catalyst used is significant and appears difficult to regenerate in order to reuse. Furthermore, the byproducts formed, in particular butanediols, are difficult to separate from the desired product. In particular, the industrially favorable method of distillation for separation (purification) purposes is extremely difficult to apply as the byproducts have very similar boiling points to the final product, and the desired product may react further, as illustrated in US2014/0039224 A1 and U.S. Pat. No. 5,393,542 B1.

The hydroformylation route is a two-step process wherein glycolaldehyde is prepared from formaldehyde, carbon monoxide and hydrogen, followed by hydrogenation of the glycolaldehyde to ethylene glycol, as illustrated in U.S. Pat. No. 4,496,781 B1. There appears to be several extraction steps present in order to separate formaldehyde from glycolaldehyde and proceed with the hydrogenation reaction.

Therefore it is desirable to provide an alternative, improved, high yielding and industrially feasible process for the preparation of ethylene glycol from sugars. An additional advantage would be the use of greater than 67% of the sugar carbon atoms present in the final product or a commercial byproduct.

It could be conceived that ethylene glycol may be prepared via a process comprising two steps; such as the preparation of glycolaldehyde from sugars and its subsequent hydrogenation to ethylene glycol. The two steps of the proposed processes appear to be independently successful as illustrated in the following paragraphs.

It is known that sugars may be pyrolysed to obtain a pyrolysis product composition comprising oxygenate compounds such as glycolaldehyde U.S. Pat. No. 7,094,932 B2; the crude pyrolysis product composition comprises $C_1$-$C_3$ oxygenate compounds, including formaldehyde, glycolaldehyde, glyoxal, pyruvaldehyde and acetol. The main product of this reaction is glycolaldehyde [U.S. Pat. No. 7,094,932 B2]. Water is the solvent of the reaction.

It is also known that pure glycolaldehyde may be hydrogenated to ethylene glycol in the liquid phase. U.S. Pat. No. 4,200,765 B1 discloses hydrogenation of glycolaldehyde under severe conditions: at high pressure [3000 psi (ca. 345 bar)], high temperature [150° C], with an organic solvent [N-methyl pyrrolidine] and a palladium on carbon [Pd/C] catalyst for a prolonged period [5 h]. U.S. Pat. Nos. 4,321,414 B1 and 4,317,946 B1 disclose the hydrogenation of glycolaldehyde with a homogenous ruthenium catalyst and U.S. Pat. No. 4,496,781 B1 discloses a continuous flow hydrogenation at low pressure [500 psi (ca. 35 bar)], high temperature [160° C.] with a ruthenium on carbon catalyst [Ru/C] in ethylene glycol and trace acetonitrile as solvent.

As illustrated, the two steps, pyrolysis of glucose to obtain, inter alia glycolaldehyde, and hydrogenation of pure glycolaldehyde in the liquid phase, appear to be independently feasible. However, in order for the pyrolysis product composition to be hydrogenated, laborious separation processes must be employed to remove formaldehyde from the pyrolysis product composition as formaldehyde is a known poison of hydrogenation catalysts [U.S. Pat. No. 5,210,337 B1]. U.S. Pat. No. 5,393,542 B1 discloses an exemplary purification process comprising multiple distillation steps followed by a solvent-induced precipitation to obtain a glycolaldehyde. Therefore, it is not possible to hydrogenate the product of the pyrolysis step (the pyrolysis product composition) directly as formaldehyde is present in the composition in a significant amount.

In addition to the requirement of removing formaldehyde, which would increase the number of process steps required, it would also be a great advantage industrially to use a solvent that is non-toxic, for example water. Therefore it would be a significant advantage to be able to carry out the hydrogenation step in the presence of formaldehyde, using a non-toxic solvent and in the solvent of the previous (pyrolysis) reaction.

With regard to hydrogenation of glycolaldehyde, although there is the provision of suitable reaction conditions to obtain a high yield in organic solvents, the reaction with water as a solvent appears to be less successful. U.S. Pat. No. 5,393,542 B1 discloses thermal degradation of glycolaldehyde (2-hydroxyacetaldehyde) when subjected to temperatures of 90° C. or higher and where water is the solvent.

EP 0 002 908 B1 discloses the variation in yield (conversion and selectivity) of the hydrogenation of glycolaldehyde reaction with the use of various catalysts in an aqueous solution at 110° C.: Raney Nickel [100% conversion 49.4% selectivity], 10% Pd/C [62% conversion, 61% selectivity] and 10% Pt/C [100% conversion, 73% selectivity]. An additional disadvantage of catalysts used in liquid water is the strain on the catalyst. In particular at high temperatures (>160° C.) many supports are not stable and will dissolve, degrade or the surface area is reduced; Energy & Fuels 2006, 20, 2337-2343. Hence, special catalysts are needed and the long-term catalyst performance is often problematic, consequently, the catalyst must be replaced frequently (ca. 3-6 months). Consequently, mild reaction conditions are favorable in order to ensure longevity of the catalyst on an industrial scale.

In addition, the choice of catalyst may affect the decomposition of glycolaldehyde when in the presence of the catalyst; U.S. Pat. No. 5,210,337 B1 discloses the problem of glycolaldehyde 'unzipping' to form formaldehyde and consequently poisoning the hydrogenation catalyst. It is also possible that glycolaldehyde may self-condense or condense with another $C_1$-$C_3$ oxygenate compounds, also illustrated in U.S. Pat. No. 5,210,337 B1. Additionally, the choice of catalyst and stability of the glycol product may affect the degree of reduction of the glycolaldehyde. It is possible that a catalyst may reduce the glycolaldehyde to ethanol or ethane, i.e. over reduce the glycolaldehyde.

Additionally, it is known that an increase in temperature, concentration of the substrate and amount and identity of catalyst present affects the yield (conversion and selectivity) of hydrogenation reactions of glycolaldehyde. Handbook of Heterogeneous Catalytic Hydrogenation for Organic Synthesis, Shigeo Nishimura, ISBN: 978-0-471-39698-7, April 2001.

As demonstrated, an industrial scale process for preparing ethylene glycol from monosaccharides via pyrolysis of monosaccharides and subsequent hydrogenation in the liquid phase is hindered from two perspectives. The first is the requirement to remove formaldehyde from the pyrolysis product composition in order to enable successful hydrogenation. The second is the provision of mild reaction conditions that are high yielding. These two disadvantages are with respect to liquid phase hydrogenation reactions.

Consequently, it is desirable to provide a high yielding two-step process that is more efficient than known processes; utilizes non-toxic solvents and cheaper catalysts; reduces byproduct production; enables purification on an industrial scale; and is unaffected by the presence of additional compounds such as formaldehyde. The ability to separate byproducts from the ethylene glycol product enables the ethylene glycol to be used in processes such as polymer production. Polymer production requires substrates to be in a highly pure form. All of these desirable aspects enable improved processes that are more attractive industrially and enable processes to become commercially feasible.

It has now been discovered that glycolaldehyde may be hydrogenated when the hydrogenation process is in the gas phase. A significant advantage is that the gas phase hydrogenation process will proceed in the presence of formaldehyde. The gas phase hydrogenation process has several further advantages, namely that it is high yielding, more efficient in comparison to solely liquid phase processes, proceeds in the presence of water and with reduced 1,2-butanediol production compared to hydrogenolysis processes.

A further significant advantage is that the yield of the commercially valuable propylene glycol byproduct is increased. This has two consequences: firstly, a larger amount of a commercially valuable byproduct is formed; secondly, it is thought that the higher yield of propylene glycol byproduct could affect the yield of alternative byproducts, such as 1,2-butanediol, consequently providing a product composition that is more easily purified.

A further advantage is the type of catalyst used. Catalysts comprising metals such as copper and nickel are significantly cheaper than catalysts comprising noble metals; consequently, the use catalysts comprising metals such as copper and nickel reduce production costs.

A further advantage is the possibility of directly hydrogenating the pyrolysis product composition obtainable from the pyrolysis of sugars without condensation of the product composition. The advantage enables a significant increase in process efficiency for the preparation of ethylene glycol from sugars.

DISCLOSURE OF THE INVENTION

The present invention provides a process for the preparation of ethylene glycol wherein a gas phase composition comprising $C_{1-3}$-oxygenate compounds is hydrogenated in the presence of a catalyst to obtain a gas phase hydrogenation product composition.

Gas phase composition means that the composition comprising $C_{1-3}$-oxygenate compounds to be hydrogenated (reduced) is in the gas phase during the hydrogenation process. It may be possible that the composition comprising $C_{1-3}$-oxygenate compounds is introduced into the reaction vessel in a phase other than the gas phase; however, the contact of the compounds with the catalyst occurs when the compounds are in the gas phase.

$C_1$-$C_3$ oxygenate compounds means oxygenated compounds comprising a carbon chain length of one, two or three carbon atoms. For example, $C_1$ oxygenate compounds comprise a carbon chain length of one carbon atom, such as formaldehyde and formic acid; $C_2$ oxygenate compounds comprise a carbon chain length of two carbon atoms, such as glycolaldehyde, glyoxal and acetic acid; $C_3$ oxygenate compounds comprise a carbon chain length of three carbon atom, such as pyruvaldehyde and acetol. $C_1$-$C_3$ oxygenate compound composition means a composition comprising one or more compounds selected from the group consisting of formaldehyde, formic acid, glycolaldehyde, glyoxal, acetic acid, pyruvaldehyde and acetol. For example, $C_1$-$C_3$ oxygenate compounds includes a composition comprising $C_2$-oxygenate compounds and may comprise $C_2$-oxygenate compounds only. A composition comprising $C_2$-oxygenate compounds means a composition comprising one or more compounds selected from the group consisting of glycolaldehyde and glyoxal. $C_2$-oxygenate compounds means oxygenated compounds comprising a carbon chain length of two carbon atoms, for example, glycolaldehyde (2hydroxyacetaldehyde) and glyoxal. A composition comprising $C_2$-oxygenate compounds may be obtainable by pyrolysis of sugars or may be a solution comprising glycolaldehyde, glyoxal or glycolaldehyde and glyoxal. Where the composition comprising $C_{1-3}$-oxygenate compounds is obtainable by pyrolysis of sugars, typically, the $C_2$-oxygenate compound component of the composition comprising $C_1$-$C_3$ oxygenate compounds is for example 10 wt % or greater, 30 wt % or greater. It is an embodiment of the present invention that the gas phase composition comprising $C_{1-3}$-oxygenate compounds comprises formaldehyde.

In a first embodiment of the invention the composition comprising $C_{1-3}$-oxygenate compounds is present in the gas phase by virtue of the method of its preparation. For example, the composition comprising $C_{1-3}$-oxygenate compounds is obtainable from the pyrolysis of sugars (prepared according to U.S. Pat. No. 7,094,932 B2), and is used directly in the following hydrogenation reaction. I.e. the product of the pyrolysis of monosaccharides is not condensed prior to the following gas phase hydrogenation reaction; however, the product may be conditioned (e.g. filtered to remove solids).

In a second embodiment of the invention the composition comprising $C_{1-3}$-oxygenate compounds obtainable by pyrolysis of monosaccharides is present in the liquid phase and brought into the gas phase in order to hydrogenate. For example, the composition comprising $C_{1-3}$-oxygenate compounds is obtainable from the pyrolysis of monosaccharides (prepared according to U.S. Pat. No. 7,094,932 B2) and is condensed to a liquid composition according to the U.S. Pat. No. 7,094,932 B2 disclosure. The liquid composition is brought into the gas phase and hydrogenated; i.e. the product of the pyrolysis of sugars is condensed prior to being brought into the gas phase and following hydrogenation. The liquid phase composition comprising $C_{1-3}$-oxygenate compounds may be in the crude or a purified form prior to being brought into the gas phase.

In order to bring the composition comprising $C_{1-3}$-oxygenate compounds into the gas phase the composition comprising $C_{1-3}$-oxygenate compounds is introduced into the reaction vessel, for example, via a nozzle that allows the dispersion of the composition comprising $C_{1-3}$-oxygenate compounds. Any compounds that are introduced into the reaction vessel in a phase other than the gas phase is converted to the gas phase by heat.

In a third embodiment of the invention, a solution of a composition comprising $C_{1-3}$-oxygenate compounds is brought into the gas phase and hydrogenated.

Hydrogenated or hydrogenation means that the composition comprising $C_{1-3}$-oxygenate compounds is subjected to hydrogenation reaction conditions. For example, the composition comprising $C_{1-3}$-oxygenate compounds is subjected to a catalyst and hydrogen wherein the substrate is reduced, e.g. glycolaldehyde is reduced to obtain ethylene glycol. Examples of conventional reaction schemes and conditions of hydrogenation reactions are disclosed in Ullmann's Encyclopaedia of Industrial Chemistry: Hydrogenation and Dehydrogenation.

Catalyst means a catalyst comprising a metal. Exemplary catalysts are disclosed in Handbook for Heterogeneous Catalytic Hydrogenation for Organic Synthesis by Shigeo Nishimura. Exemplary gas phase hydrogenation catalysts include a heterogeneous catalyst comprising a one or more metals selected from the group consisting of Cu, Ni, Co, Mo, Fe, Pt, Pd, Ru, Rh, Ir, preferably copper or nickel. The catalyst may further comprise a support; the support may comprise of for example, carbon, silica, alumina, silicon carbide, titania and zirconia. Examples of a catalyst include copper on a carbon support, copper on a silica support, copper on an alumina support, copper on a silicon carbide support, copper on a titania support, copper on a zirconia support, nickel on a carbon support, nickel on a silica support, nickel on an alumina support, nickel on a silicon carbide support, nickel on a titania support, nickel on a zirconia support, platinum on a carbon support, platinum on a silica support, platinum on an alumina support or platinum on a silicon carbide support.

Gas phase hydrogenation product composition means a composition comprising ethylene glycol obtainable by the hydrogenation of a gas phase composition comprising $C_{1-3}$oxygenate compounds. The gas phase hydrogenation product composition may also comprise propylene glycol and methanol; i.e. the reduced products of $C_{1-3}$-oxygenate compounds including formaldehyde, pyruvaldehyde and acetol. The gas phase hydrogenation product composition may also comprise unreacted $C_2$-oxygenate compounds, i.e. glycolaldehyde. The first product composition may also comprise unreacted or semi-reduced $C_{1-3}$-oxygenate compounds, i.e. formaldehyde, glycolaldehyde, glyoxal, pyruvaldehyde, acetol.

The product of the present invention may be the product composition obtainable or obtained from the gas phase hydrogenation comprising ethylene glycol obtainable by the gas phase hydrogenation reaction. Alternatively, the product of the present invention may be the gas phase hydrogenation product composition that has been purified. Alternatively, the product of the present invention may be the product of the gas phase hydrogenation product composition that has been further hydrogenated, e.g. in the liquid phase, to obtain a subsequent, liquid phase hydrogenation product composition. Alternatively, the product of the present invention may be the subsequent, liquid phase hydrogenation product composition that has been purified.

Sugar means one or more sugars selected from monosaccharides and disaccharides. Preferably, sugar means one or more sugars selected from the group consisting of glucose, sucrose, fructose, xylose, mannose, arabinose and galactose. Preferably the sugar is glucose. The sugar may be in the form of a solution, wherein the sugar solution comprises a monosaccharide and a solvent. The solvent of the monosaccharide solution is a solvent selected from the group consisting of: water or water and alcohol. Alcohol means one or more alcohol selected from the group consisting of methanol and ethanol. For example, the sugar solution may be present as an aqueous sugar solution, preferably an aqueous glucose solution.

An aspect of the present invention is the temperature of the hydrogenation reaction. The composition comprising $C_{1-3}$oxygenate compounds is hydrogenated at a temperature from 150° C. to 350° C., from 150° C. to 300° C., from 200° C. to 300° C., from 200° C. to 280° C.

An aspect of the present invention is the pressure of the hydrogenation reaction. The composition comprising $C_{1-3}$oxygenate compounds is hydrogenated at a pressure from 0.1 bar to 30 bar, from 0.1 to 5 bar.

An aspect of the present invention is the reduction in the amount of formaldehyde present in the composition comprising $C_{1-3}$-oxygenate compounds during the gas phase hydrogenation process. The formaldehyde is reduced in order for a subsequent liquid phase hydrogenation to be successful. The formaldehyde is reduced in order for a subsequent liquid phase hydrogenation to produce a yield of at least 50% ethylene glycol from the hydrogenation of the first product composition.

A further aspect of the present invention is the yield of ethylene glycol from $C_2$-oxygenate compounds prepared by the gas phase hydrogenation of a composition comprising $C_{1-3}$oxygenate compounds is equal to or greater than 50%, equal to or greater than 60% equal to or greater than 70% equal to or greater than 75%.

A further aspect of the present invention is the yield of propylene glycol and acetol from $C_3$-oxygenate compounds prepared by the gas phase hydrogenation of a composition comprising $C_{1-3}$-oxygenate compounds is equal to or greater than 30%, equal to or greater than 35% equal to or greater than 40%.

An embodiment of the present invention is the hydrogenation of the gas phase hydrogenation product composition prepared by the gas phase hydrogenation of a composition comprising $C_{1-3}$-oxygenate compounds. The gas phase hydrogenation product composition may be subsequently hydrogenated in the presence of a catalyst and a solvent; a subsequent, liquid phase hydrogenation product composition is obtained. i.e. the subsequent hydrogenation process may be a liquid phase process.

The solvent is a solvent selected from the group consisting of: water; alcohol or water and alcohol. Alcohol means one or more alcohol selected from the group consisting of methanol, ethanol, ethylene glycol and propylene glycol. The solvent may be a mixture of water and alcohol. Where the solvent is water and alcohol, the water and alcohol are in a ratio of equal to or greater than 95:5, 90:10, 80:20, 70:30, 60:40, 50:50, 40:60 and 30:70.

The optional, subsequent liquid phase hydrogenation process is carried out in the presence of a heterogenous catalyst comprising a catalyst metal component such as ruthenium, ruthenium alloy, palladium or nickel. The catalyst metal component is supported by a support such as carbon. Known hydrogenation catalysts include ruthenium on a carbon support. For example, the subsequent liquid phase hydrogenation process may be carried out in the presence of a catalyst such as ruthenium on a carbon support catalyst. For example, the subsequent liquid phase hydrogenation process may be carried out in the presence of catalyst such as a 5% or 10% ruthenium on a carbon support catalyst. Examples of ruthenium alloy catalysts comprising 0.5-2% ruthenium are disclosed in WO 2014/066052 A1.

The liquid phase hydrogenation process catalyst may be present in the reaction solution in a wt/wt ratio of formaldehyde:catalyst metal component of from 1:1 to 15:1, from 1:1 to 11:1; from 1:1 to 10:1; from 1:1 to 7:1; from 1:1 to 5:1; from 3.0:1 to 15:1; from 3.1:1 to 15:1; from 3.2:1 to 15:1. Preferably, the liquid phase hydrogenation process catalyst is present in the reaction solution in a wt/wt ratio of formaldehyde:catalyst metal component of from 1:1 to 15:1, from 1:1 to 11:1; from 1:1 to 10:1; from 1:1 to 7:1; from 1:1 to 5:1; from 3.0:1 to 15:1; from 3.1:1 to 15:1; from 3.2:1 to 15:1.

The subsequent liquid phase hydrogenation process may be carried out at a pressure of from about 10 bar to 90 bar, from 10 bar to 120 bar, from 10 bar to 150 bar. Preferably, the subsequent liquid phase hydrogenation process is carried out at a pressure of from about 10 bar to 90 bar, from 10 bar to 120 bar, from 10 bar to 150 bar.

The subsequent liquid phase hydrogenation process may be carried out at a temperature of from 40 to 160° C., from 50 to 140° C., from 60 to 130° C., preferably from 80 to 120° C. Preferably, the subsequent liquid phase hydrogenation process is carried out at a temperature of from 40 to 160° C., from 50 to 140° C., from 60 to 130° C., preferably from 80 to 120° C.

The yield of ethylene glycol for the subsequent liquid phase hydrogenation process is equal to or greater than 80%, greater than 85%, greater than 90%, greater than 95%.

The yield of propylene glycol for the subsequent liquid phase hydrogenation process is equal to or greater than 80%, greater than 85%, greater than 90%, greater than 95%.

The total yield of ethylene glycol for the gas phase hydrogenation process and the subsequent liquid phase hydrogenation process is equal to or greater than 70%, greater than 75%, greater than 80%, greater than 85%.

The total yield of propylene glycol for the gas phase hydrogenation process and the subsequent liquid phase hydrogenation process is equal to or greater than 70%, greater than 75%, greater than 80%, greater than 82%.

An aspect of the present invention is the duration of the process for hydrogenation of the composition comprising $C_{1-3}$-oxygenate compounds. The duration of the hydrogenation of the product composition is 6.0 hours or less, 3.0 hours or less, 2.5 hours or less, 2.0 hours or less, 1.0 hour or less, 0.5 hours (30 mins) or less, 15 mins or less. It is an embodiment of the present invention to reduce the duration of the hydrogenation of compositions comprising $C_{1-3}$-oxygenate compounds through gas phase hydrogenation or gas phase hydrogenation with subsequent liquid phase hydrogenation, compared to a solely liquid phase hydrogenation process. A reduction in duration of the hydrogenation of compositions comprising $C_{1-3}$-oxygenate compounds process is illustrated by the batch conditions provided. Continuous flow processes correspond to batch conditions, however, variables such as temperature, pressure, and amount of catalyst present affect the duration of the process. It is intended that the reduction in duration of the hydrogenation process according to the present invention is transferable when comparing liquid phase hydrogenation to either gas phase or gas phase followed by liquid phase.

An embodiment of the present invention is purification of the product of the subsequent liquid phase hydrogenation process (purification of the subsequent product composition). For example the subsequent liquid phase product composition is purified.

Both the gas and liquid phase product compositions comprise a 1,2-butanediol (1,2-BDO):ethylene glycol wt/wt ratio equal to or less than 0.01:1, 0.008:1, 0.0075:1, 0.005:1, 0.004:1, 0.003:1.

An embodiment of the present invention is a two-step process. 'Two step' process means the conversion of sugars to ethylene glycol via two chemical transformations: the pyrolysis of sugars and the hydrogenation of glycolaldehyde obtainable from the pyrolysis of glucose. The two-step process of the present invention is the pyrolysis of monosaccharides to obtain a composition comprising $C_{1-3}$-oxygenate compounds followed by a gas phase hydrogenation process and optionally a subsequent liquid phase hydrogenation process. For example the crude pyrolysis product composition is hydrogenated directly, first in the gas phase then in the liquid phase. Alternatively, the number of process steps may be considered to be the number of reactions of the total process. In this understanding the process would be a two or three step process as there is one pyrolysis reaction followed by either one (gas phase) or two (gas and liquid phase) hydrogenation reactions.

Purifying means separating the specific chemical compounds of the (hydrogenated) product composition obtainable by the hydrogenation process of the present invention. I.e. purifying means the separation of ethylene glycol, propylene glycol and other compounds of the (hydrogenated) product composition. Exemplary separation processes are disclosed in U.S. Pat. No. 8,177,980 B2 and US 2014/0039224 A1. Such separation (purification) processes may be chromatography and distillation.

Ethylene glycol prepared according to the present invention may be used as a chemical. For example, ethylene glycol may be used as a monomer in the preparation of polymers including polyethylene terephthalate (PET), polyester resins, fibers and films. Ethylene glycol may also be used as a deicing agent, coolant, in particular in refrigeration apparatus, antifreeze agent or solvent. As described on: http://www.dow.com/ethyleneglycol/prod/meg.htm

EXAMPLES

Example 1

A pyrolysis product composition comprising $C_1$-$C_3$ oxygenate compounds was obtained by pyrolysis of a 20 wt % aqueous glucose (D-glucose monohydrate; Sigma Aldrich) solution as described in U.S. Pat. No. 7,094,932 B2. The typical composition of the pyrolysis product composition is provided in Table 1.

TABLE 1

Composition of the pyrolysis product composition of Example 1

| | GLA | GLO | PYR | FOR | ACE | EG | PG | MeOH |
|---|---|---|---|---|---|---|---|---|
| Example 1 | 145.9 g/l | 5.4 g/l | 17.8 g/l | 16.5 g/l | 5.7 g/l | — | — | — |

GLA = Glycolaldehyde
GLO = Glyoxal
PYR = Pyruvaldehyde
FOR = Formaldehyde
ACE = Acetol
EG = Ethylene glycol
PG = Propylene glycol
MeOH = Methanol

Example 2

Liquid Phase Hydrogenation with 10% Cu/C Catalyst, 6 Hours

The pyrolysis product composition of Example 1 [described in Table 1] (15.5 g) was loaded into an autoclave along with 10% Cu on carbon (10% Cu/C) catalyst (Sulfusorb 12 from Calgon Carbon, 0.40 g). Prior to catalyst loading, the catalyst was activated at 300° C. for 2 hours in a flow of 5% hydrogen in nitrogen. The autoclave was purged 3 times with hydrogen and subsequently pressurized to 90 bars with hydrogen. The mixture was heated to 80° C. from room temperature over the course of 15 min and stirred at 80° C. for 6 hours. The autoclave was then cooled to room temperature and the decrease in hydrogen pressure was noted.

The hydrogenated product mixture was isolated from the catalyst by filtration and analyzed by HPLC and GC.

The maximum theoretical yield of ethylene glycol was based on hydrogenation of both glyoxal and glycolaldehyde to ethylene glycol. The maximum theoretical yield of propylene glycol was based on hydrogenation of pyruvaldehyde and acetol to propylene glycol.

The yield of ethylene glycol was <2% and the yield of propylene glycol was <2%.

The conversion of glycolaldehyde was 12.1%.

Example 2 demonstrates that the pyrolysis product composition is not significantly hydrogenated in the liquid phase by a Cu/C catalyst at 80° C. for 6 hours.

Example 3

Liquid Phase Hydrogenation with 5% Ru/C Catalyst, 2 Hours

The pyrolysis product composition of Example 1 and described in Table 1 (15.5 g) was loaded into an autoclave along with 5% Ru on carbon (5% Ru/C) catalyst (Sigma Aldrich, 0.20 g). The autoclave was purged 3 times with hydrogen and subsequently pressurized to 90 bars with hydrogen. The mixture was heated to 80° C. from room temperature over the course of 15 min and stirred at 80° C. for 2 hours. After reaction the autoclave was cooled to room temperature and the decrease in hydrogen pressure was noted.

The hydrogenated product mixture was isolated from the catalyst by filtration and analyzed by HPLC and GC.

The maximum theoretical yield of ethylene glycol was based on hydrogenation of both glyoxal and glycolaldehyde to ethylene glycol. The maximum theoretical yield of propylene glycol was based on hydrogenation of pyruvaldehyde and acetol to propylene glycol.

The yield of ethylene glycol was 12% and the yield of propylene glycol was <1% (acetol is formed).

The conversion of glycolaldehyde was 14%.

Conversion means the transformation of $C_2$-oxygenate compounds to another compound or compounds. Selectivity means the transformation of $C_2$-oxygenate compounds to ethylene glycol rather than other compounds such as ethanol or ethane.

Example 3 demonstrates that the pyrolysis product composition is not significantly hydrogenated in the liquid phase by a 5% Ru/C catalyst at 80° C. for 2 hours.

Example 4

Gas Phase Hydrogenation with 10% Cu/C Catalyst

A pyrolysis product composition comprising $C_1$-$C_3$ oxygenate compounds was obtained by pyrolysis of a 20 wt % aqueous glucose (D-glucose monohydrate; Sigma Aldrich) solution as described in U.S. Pat. No. 7,094,932 B2. Prior to condensation of the pyrolysis product composition, the composition was hydrogenated in the gas phase. The hydrogenation was performed in a fixed bed reactor loaded with a 10 wt % Cu on Carbon catalyst (Sulfusorb 12 from Calgon Carbon). The catalyst had been activated in situ at 300° C. for 2 hours in a flow of hydrogen. Before entering the hydrogenation reactor, the pyrolysis product composition was mixed with hydrogen to give a partial pressure of hydrogen of 0.46 atm. (corresponding to a $H_2$:C ratio of 50). The pyrolysis product composition was hydrogenated at 230° C. with a residence time in the reactor of 0.15 seconds to obtain a first product composition The typical composition of the pyrolysis product composition is given in Table 1; Example 1.

The yield of ethylene glycol was 79%. The yield of propylene glycol was 41%.

A 77% reduction of formaldehyde originally present in the pyrolysis product composition was observed.

TABLE 2

Composition of the gas phase hydrogenation product composition prepared according to Example 4.

| | GLA | GLO | PYR | FOR | ACE | EG | PG | MeOH |
|---|---|---|---|---|---|---|---|---|
| Example 1 | 145.9 g/l | 5.4 g/l | 17.8 g/l | 16.5 g/l | 5.7 g/l | — | — | — |
| Example 4 | 12.2 g/l | — | — | 3.8 g/l | 14.2 g/l | 120.4 g/l | 5.9 g/l | 5.5 g/l |

GLA = Glycolaldehyde
GLO = Glyoxal
PYR = Pyruvaldehyde
FOR = Formaldehyde
ACE = Acetol
EG = Ethylene glycol
PG = Propylene glycol
MeOH = Methanol Example 4 demonstrates that hydrogenation of a pyrolysis product composition in the gas phase over a 10% Cu/C catalyst (Sulfusorb 12 from Calgon Carbon) at 230° C. is extremely successful. Example 4 demonstrates that it is possible to retain glycolaldehyde in the gas phase at a high temperatures (230° C.), and hydrogenate the pyrolysis product composition with a catalyst that is ineffective in the liquid phase (Cu/C).

Example 5

Liquid Phase Hydrogenation of the First Product Composition of Example 4 with 5% Ru/C Catalyst, 2 Hours The gas phase hydrogenation product composition (15.5 g) described in Table 2 Example 4, was loaded into an autoclave along with 5% Ru on carbon catalyst (Sigma Aldrich, 0.20 g). The autoclave was purged 3 times with hydrogen and subsequently pressurized to 90 bars with hydrogen. The mixture was heated to 80° C. from room temperature over the course of 15 min and stirred at 80° C. for 2 hours. After reaction the autoclave was cooled to room temperature and the decrease in hydrogen pressure was noted. A liquid phase hydrogenation product composition was obtained.

The liquid phase hydrogenation product composition (the product of Example 5) was isolated from the catalyst by filtration and analyzed by HPLC and GC.

The maximum theoretical yield of ethylene glycol was based on hydrogenation of glycolaldehyde into ethylene glycol and the maximum theoretical yield of propylene glycol was based on hydrogenation of acetol into propylene glycol.

The yield of ethylene glycol was ≥98% and the yield of propylene glycol was ≥98%.

Conversion of glycolaldehyde was 100%.

The total yield of ethylene glycol from gas phase hydrogenation (Example 4) followed by liquid phase hydrogenation (Example 5) was ≥89% and the total yield of propylene glycol was ≥84%.

Example 5 demonstrates that hydrogenation of the pyrolysis product composition in the gas phase (prior to condensation) greatly improves a subsequent liquid phase hydrogenation step in comparison to hydrogenation with either Cu/C or Ru/C catalysts in the liquid phase only (Examples 2 and 3).

Example 5 also demonstrates that high ethylene glycol yields are obtainable by the two-step (gas and subsequent liquid phase hydrogenation reactions). Additionally, an excellent yield of propylene glycol is obtainable.

Example 6

Liquid Phase Hydrogenation of Pyrolysis Product Composition with 5% Ru/C Catalyst, 6 Hours The pyrolysis product composition of Example 1 and described in Table 1 (15.5 g) was loaded into an autoclave along with 5% Ru on carbon catalyst (Sigma Aldrich, 0.40 g). The autoclave was purged 3 times with hydrogen and subsequently pressurized to 90 bars with hydrogen. The mixture was heated to 80° C. from room temperature over the course of 15 min and stirred at 80° C. for 6 hours. After reaction the autoclave was cooled to room temperature and the decrease in hydrogen pressure was noted.

The liquid phase hydrogenated product composition was isolated from the catalyst by filtration and analyzed by HPLC and GC.

The maximum theoretical yield of ethylene glycol was based on hydrogenation of both glyoxal and glycolaldehyde into ethylene glycol and the maximum theoretical yield of propylene glycol was based on hydrogenation of pyruvaldehyde and acetol into propylene glycol.

The yield of ethylene glycol was 81% and the yield of propylene glycol was 57%.

Conversion of glycolaldehyde was 100%.

Example 6 demonstrates that the pyrolysis product composition is hydrogenated in the liquid phase by a 5% Ru/C catalyst; however, longer reaction times [6 hours compared to 2 hours (Example 5)] and an increased amount of catalyst are required [0.4 g compared to 0.2 g (Example 5)]. Furthermore the selectivity is decreased compared to both Examples 4 and 5.

TABLE 3

Summary of Experimental Results for Examples 2-6.

| Ex | Catalyst | Phase | TC (h) | P (bar) | T (° C.) | EG (wt/wt %) | PG (wt/wt %) | Conversion of $C_2$-oxygenate compounds to EG |
|---|---|---|---|---|---|---|---|---|
| 2 | 10% Cu/C | Liquid | 6 | 90 | 80 | <2% | <2% | 12.1% |
| 3 | 5% Ru/C | Liquid | 2 | 90 | 80 | 12% | <1% | 14% |
| 4 | 10% Cu/C | Gas | N/A | 1 | 230 | 77% | 24% | 91.9% |
| 5 | 5% Ru/C | Liquid | 2 | 90 | 80 | 89* | 84* | 100% |
| 6 | 5% Ru/C | Liquid | 6 | 90 | 80 | 81% | 57% | 100% |

*The yield provided for Example 5 are the combined yields of Examples 4 and 5. The yield of reaction 5 is >98% for both ethylene glycol and propylene glycol.

The invention claimed is:

1. A process for gas-phase preparation of ethylene glycol, comprising contacting a $C_{1-3}$-oxygenate gaseous feed composition with a catalyst and hydrogen in the gas phase, and producing a product composition comprising $C_1$-$C_3$ glycols, optionally, further hydrogenating the product composition.

2. A process according to claim 1, wherein the feed composition comprises glycolaldehyde.

3. A process according to claim 1, wherein the feed composition further comprises at least one oxygenate compound selected from the group consisting of formaldehyde, glycolaldehyde, glyoxal, pyruvaldehyde and acetol.

4. A process according to claim 1, wherein the catalyst comprises a metal component selected from one or more of the group consisting of Cu, Ni, Co, Mo, Fe, Pt, Pd, Ru, Rh, and Ir.

5. A process according to claim 1, wherein the catalyst comprises a support selected from one or more of the group consisting of carbon, silica, alumina, silicon carbide, titania, and zirconia.

6. A process according to claim 1, wherein the feed composition comprises $C_2$-oxygenate compounds which are hydrogenated at a temperature from 150° C. to 350° C.

7. A process according to claim 6, wherein the feed composition comprises $C_2$-oxygenate compounds which are hydrogenated at a pressure from 0.1 bar to 30 bar.

8. A process according to claim 1, wherein the product composition is subsequently hydrogenated in the presence of a catalyst, hydrogen and a solvent to produce a product stream.

9. A process according to claim 8, wherein the solvent is selected from the group consisting of water, alcohol and water and alcohol.

10. A process according to claim 9, wherein the alcohol is selected from one or more of the group consisting of methanol, ethanol, ethylene glycol and propylene glycol.

11. A process according to claim 8, wherein the catalyst for the subsequent hydrogenation comprises a metal component selected from the group consisting of ruthenium, ruthenium alloy, palladium, platinum and nickel.

12. A process according to claim 8, wherein the product stream is purified.

13. A process according to claim 1, wherein propylene is produced at a yield of 50% or greater.

14. A process according to claim 1, wherein 1,2-butanediol and ethylene glycol are produced in a wt/wt ratio equal to or less than 0.01:1.

15. A process according to claim 1, wherein the $C_{1-3}$-oxygenate feed composition further comprise one or more oxygenate compounds selected from the group consisting of glycolaldehyde and glyoxal.

16. A process for the preparation of ethylene glycol in the gas phase, comprising:
pyrolysing a sugar to obtain a pyrolysis product comprising $C_{1-3}$-oxygenate compounds; followed by hydrogenating the pyrolysis product comprising the $C_{1-3}$-oxygenate compounds according claim 1.

17. The process according to claim 16, wherein the sugar is one or more compounds selected from the group consisting of glucose, sucrose, fructose, xylose, mannose, arabinose and galactose.

18. The process according to claim 16, wherein the pyrolysis product comprising $C_{1-3}$-oxygenate compounds comprises at least formaldehyde and one or more oxygenate compounds selected from the group consisting of glycolaldehyde, glyoxal, pyruvaldehyde and acetol.

19. The process according to claim 16, wherein the pyrolysis product comprising $C_{1-3}$-oxygenate compounds comprises at least 10 wt % $C_2$-oxygenate compound.

20. The process according to claim 16, wherein the pyrolysis product is hydrogenated without prior condensation of the pyrolysis product.

21. The process according to claim 1, wherein the feed composition comprises formaldehyde.

22. The process according to claim 2, wherein the feed composition further comprises formaldehyde.

* * * * *